United States Patent
Raghavan et al.

(10) Patent No.: US 6,933,372 B2
(45) Date of Patent: Aug. 23, 2005

(54) METHOD TO PRODUCE A SOLID FORM OF HEPARIN

(75) Inventors: Ranganatha Raghavan, Dayton, OH (US); Jay Lee Jett, Bellbrook, OH (US)

(73) Assignee: Warner-Lambert Company, Morris Plains, NJ (US)

(*) Notice: Subject to any disclaimer, the term of this patent is extended or adjusted under 35 U.S.C. 154(b) by 0 days.

(21) Appl. No.: 10/789,466

(22) Filed: Feb. 27, 2004

(65) Prior Publication Data

US 2004/0176581 A1 Sep. 9, 2004

Related U.S. Application Data

(60) Provisional application No. 60/452,701, filed on Mar. 7, 2003.

(51) Int. Cl.[7] .................. C08B 37/10; C08B 37/00; C07H 5/06; C07H 5/04
(52) U.S. Cl. .................. 536/21; 536/55.3; 536/55.2; 536/55.1
(58) Field of Search .................. 536/21, 55.3, 55.2, 536/55.1

(56) References Cited

U.S. PATENT DOCUMENTS

| 2,034,599 | A | | 3/1936 | Van Marle et al. |
| 2,571,679 | A | | 10/1951 | Butturini et al. |
| 2,797,184 | A | | 6/1957 | Coleman et al. |
| 2,884,358 | A | | 4/1959 | Bush et al. |
| 2,954,321 | A | | 9/1960 | Coleman et al. |
| 3,330,327 | A | * | 7/1967 | Kennedy et al. ......... 159/49 |
| 3,337,409 | A | | 8/1967 | Williams |
| 3,817,831 | A | | 6/1974 | Mancilla et al. |
| 4,510,135 | A | * | 4/1985 | Teng ................ 514/56 |
| 4,816,446 | A | * | 3/1989 | Feller et al. ........... 514/56 |
| 5,626,904 | A | * | 5/1997 | Frederiksen ........... 426/649 |
| 5,912,237 | A | * | 6/1999 | Kennedy ............... 514/56 |
| 6,090,928 | A | | 7/2000 | Donges et al. |
| 6,232,093 | B1 | | 5/2001 | VanHoudenhoven et al. |
| 6,485,945 | B1 | | 11/2002 | Potter et al. |

FOREIGN PATENT DOCUMENTS

| CN | 1218058 A | | 6/1999 | |
| CN | 1218058 A | * | 6/1999 | ......... C08B/37/10 |
| EP | 0 712 864 B1 | | 10/1995 | |
| EP | 0 737 692 B1 | | 4/1996 | |
| WO | WO80/01383 | | 7/1980 | |
| WO | WO9521198 A1 | | 8/1995 | |
| WO | WO0157092 A1 | | 8/2001 | |

OTHER PUBLICATIONS

R. Simon (Dryers) LTD website□□http://www.simon-dryers.co.uk/drum/index.htm (1998).*
Martin et al. Physical Pharmacy, Fourth edition. Lea & Fediger 1993 p. 29.*
Ma Ting, et al., "Processing Technology of Anticoagulative material added in superfine CaCO3 Powder", XP002283000, Database accession No. EIX099454800206 abstract, Database compendex 'Online! Engineering Information, Inc., New York, NY, US.

* cited by examiner

Primary Examiner—James O. Wilson
Assistant Examiner—Matthew L. Fedowitz
(74) Attorney, Agent, or Firm—Christine S. Lee; Charles W. Ashbrook

(57) ABSTRACT

The present invention provides a new method to process a solution containing heparin; heparin salts or heparin complexes in a solvent or a mixture of solvents to a solid form of heparin products characterized by use of a drum dryer at atmospheric pressure or under vacuum and at a suitable drying temperature.

17 Claims, No Drawings

METHOD TO PRODUCE A SOLID FORM OF HEPARIN

The present application claims priority under 35 USC section 119(e) to U.S. Provisional Application No. 60/452,701, filed Mar. 7, 2003.

FIELD OF THE INVENTION

The present invention provides a new method to process a solution containing heparin, heparin salts or heparin complexes in a solvent or a mixture of solvents to a solid form of heparin products characterized by use of a drum dryer at atmospheric pressure or under vacuum and at a suitable drying temperature.

BACKGROUND OF THE INVENTION

Heparin, heparin salts and heparin complexes, referred to as "heparin" herein, are used broadly in healthcare as blood anticoagulants, antithrombotic agents and coating agents for medical devices. Heparin salts are also used as starting materials to produce low molecular weight heparin, e.g. Fragmin® (Dalteparin Sodium) [WO 80/01383]. Heparin can be extracted from animal tissues and organs and typically contains several biologically derived impurities such as proteins and glycosoaminoglycans such as Dermatan Sulfate. Numerous extraction processes have been developed, e.g. those disclosed in U.S. Pat. Nos. 2,571,679, 2,954,321, 3,337,409, 6,232,093B1 and references cited therein.

To produce the solid form of heparin, in a typical heparin manufacturing and purification process, heparin is precipitated from its water solution with a large volume of a water miscible organic solvent, e.g., ethanol [U.S. Pat. Nos. 2,571,679, 2,954,321], methanol [U.S. Pat. Nos. 2,884,358, 2,797,184, 3,337,409], acetone [U.S. Pat. No. 2,954,321] and the like. The precipitated heparin is dehydrated with a water miscible solvent or collected by filtration, and thereafter dried under vacuum mostly at about 40–75° C. Other drying methods are also used to dry the heparin precipitate as a reconstituted paste in water followed by freeze-drying, e.g. lyophilization [U.S. Pat. No. 3,817,831].

A method of spray drying of a heparin solution was disclosed in a Chinese patent application, CN 1218058A (published on 1999-06-02). By atomizing the heparin solution and drying in hot air entering the spray dryer at 190–200° C., a dry powder was obtained with a specific activity of 128 u/mg.

Inherent problems exist with the method to produce a solid form of heparin in a conventional process. The most significant among these are, excessive use of potentially dangerous and flammable organic solvents, requirement of precise vacuum and temperature control during the drying process, requirement of multiple process stages that include precipitating, drying, milling, and re-drying steps, requirement of extremely long process cycle-times, requirement of high capital and operating costs, requirement of relatively long time of labor, requirement of frequent cleaning of spray nozzles, significant product losses due to handling and entrainment, and potentially adverse quality impact on this heat sensitive heparin product. Typically, in order to preserve anticoagulant properties (potency), the process temperatures cannot exceed 100° C. reach for prolonged times especially during drying stages.

Single or double drum dryers are widely used in chemical and pharmaceutical industries. These drum dryers are used for processing solutions to produce solid products in one operation, e.g. inorganic salts [U.S. Pat. No. 2,034,599], tertiary amine oxide [U.S. Pat. No. 3,330,327] and polysaccharides [U.S Pat. No. 6,485,945]. A double-drum dryer consists of two counter or co-rotating drums that are heated from the inside by steam or other suitable hot fluids. In a double drum dryer, a solution to be dried is loaded into the nip between the drums and squeezed into a thin layer on drum surfaces where it is dried by the hot drum surfaces. Knives scrape off the dried solid and collected in a hopper for further downstream processing. It can be operated under vacuum for temperature-sensitive chemicals. The residence time of this drying process is very short and takes just a few seconds. This is particularly beneficial to heat sensitive products. The drying process can be run in batches, semi-continuous or continuous modes.

SUMMARY OF THE INVENTION

This invention provides a new method to process a solution containing heparin to a solid form of heparin with a drum dryer operated at atmospheric or vacuum pressure and a suitable drying temperature. Preferably, a double drum dryer is used. The invention is further disclosed in the attached claims.

The solution processed with the invention contains heparin as a main component. It may be a solution from a heparin purification or manufacturing process, an Q extraction solution of animal mucosa, tissues or organs with contaminants, or a solution with contaminants eluted from resins absorbed heparin. Such contaminants could be, for example, glycocosaminoglycans, proteins, bacteria, dermatan sulfate, pathogens etc.

By applying the method of this invention, the production of solid heparin from its solution uses one-step operation by means of a drum dryer instead of multiple steps in a conventional extraction, production or purification process. Specifically, this invention provides excellent advantages to eliminate the requirement to use a large amount of dangerous and expensive organic solvents, to reduce the process cycle times, to allow the possibility of a continuous drying process, to improve energy efficiency and to reduce the risks of personnel safety in handling organic solvents.

DETAILED DESCRIPTION OF THE INVENTION

The present invention provides a new method of using a single or a double drum dryer, preferably a double drum dryer, to process a solution containing heparin, heparin salts or heparin complexes as a main component, preferably heparin sodium, in a solvent, such as water; or a mixture of solvents, e.g. water mixed with one or more water miscible organic solvents, e.g. alcohol (ethanol, methanol, n-propanol or isopropanol) or acetone; or alcohols in case of certain heparin complexes, e.g. heparin-benzalkonium chloride complex; to obtain a solid form of heparin products.

In a double drum dryer, the feed solution is heated in the nip between the drums and temperature until it reaches the optimum properties such as viscosity before adhering to the drum surfaces for further drying. A similar approach is taken in the case of a single drum dryer is used by preferably pre-heating the feed solution and utilizing an appropriate loading technique to dry the solution of heparin.

The process of the present invention provides a dry solid form of heparin solution in less than 1 minute from initial contact with a drum. For example, a dry solid form of heparin can be obtained from solution in less than 30 seconds.

The dried solid form of heparin can be obtained by the following procedures:

1) By using the drying method according to the invention.
2) The dried solid form of heparin, mostly in the form of flakes and powders containing acceptably low levels of volatiles and moisture, is thereafter removed from the surfaces of drums by a set of scraper blades.
3) The solid form of heparin is collected in a hopper or other type of container and sent for further processing and milling.

The concentration of the solution containing heparin to be loaded on the drum dryer can be in a range of 1% to 50% weight per volume (g/mL), preferably about 10–17% weight per volume (g/mL) concentration.

The temperature of the solution containing heparin to be loaded on the drum dryer is in a range of ambient temperature to the temperature under the solution's boiling point, preferably at the ambient temperature.

The drying temperature is in a range of 20–210° C., preferably about 130–170° C. The temperature can be regulated by adjusting the steam pressure inside the drums.

The operation pressure in the drum dryer can be in a range of vacuum (down to 0.01 mmHg) to atmospheric pressure, preferably at atmospheric pressure.

The optimal operating settings of the drum dryer depend on the particular type of dryer used and also on the concentration of the solution containing heparin being fed into the drum dryer. In general, optimal conditions for the drying process of a solution containing heparin and drum dryer, according to this invention, can be achieved by adjusting the following conditions, but not limited to, the rate of feeding, the temperature of feed solution, the rotational speed of the drums, the location of product scraper blades, surface area of the drums, operating temperature of the drum surfaces and the operating pressures in the drying hood. These optimal conditions can be determined by a person skilled in the art.

The claimed drying process is rapid. It can be performed in batch, semi-continuous or continuous modes. The quality attributes of the product dried by the method of the invention are similar or better to those made with the conventional processes. The moisture and other volatile content of the dried product usually can be less than 5% by weight.

The process of the present invention provides a dry solid form of heparin with potency of at least 100 u/mg. For example, the method of the present invention provides a dry solid form of heparin with a potency of at least 140 u/mg. In a further example the method of the present invention provides a dry solid form of heparin with a potency of at least 160 u/mg.

This process of the present invention is equally applicable to purified heparin solutions as well as solutions of crude heparin where the heparin includes protein and glycosoaminoglycan impurities. The present invention can be used to dry solutions of various, crude or fine, heparin products to obtain the corresponding solid form of the heparin products, e.g. free heparin, a salt of heparin with alkali metal, e.g. sodium, a salt of heparin with alkaline earth metal, e.g. calcium, a salt of heparin with ammonium, or a quaternary ammonium, or tertiary amine, or any organic base, a complex of heparin with a salt of a quaternary ammonium, or tertiary amine, or any organic base with an inorganic or organic acid, e.g. heparin-benzalkonium chloride complex, heparin-tridodecylmethylammonium chloride complex. The preferred use of the invention is to dry a solution of heparin sodium in a solvent or a mixture of solvents.

The present invention is useful in processing a solution containing heparin as a main component that may come from, but is not limited to, a heparin purification or manufacturing process, an extraction solution of animal mucosa, tissues or organs with contaminants, or an elution solution with contaminants eluted from resins absorbed heparin, to the heparin products that can become solid with a various purity of heparin. Such contaminants could be, for example, glycocosaminoglycans, proteins, bacteria, dermatan sulfate, pathogens etc. The method of this invention can also be scaled-up or scaled-down according to the required production rates.

The advantages of this invention provide for the use of a less amount of organic solvents so that the process becomes much safer to operate than a conventional one. Through the application of this invention, a solution containing heparin can be dried to a solid form in a single step eliminating the inherent problems of a conventional drying process. Specifically, this invention reduces the requirements of large volumes of potentially dangerous organic solvents, minimizes batch cycle times, reduces the capital and operating costs, and minimizes the labor requirements per batch.

The following examples illustrate the invention and they should not be considered as any limitation of the invention in any way.

EXAMPLES

Example 1

Drying at Atmospheric Pressure with a Double Drum Dryer

A solution (1.0 Liter) of 13% (by weight) heparin sodium and 4% (by weight) of SDA-3A Alcohol in water at ambient temperature ("purified heparin") was loaded into a Buflovake® 6"×8" Vacuum and Atmospheric Double Drum Dryer with a rotating speed of drum at 2.6 R.P.M., a steam pressure at 72.5 psig (4.96 bar, steam temperature at 159° C.), a level in NIP at approximately ⅜ inch (9.5 mm), a drum gap at 0.008 inch (0.203 mm), and a pressure in the dryer at atmospheric pressure. 0.3 lbs (131.6 g) of dried solid form of heparin sodium was collected in the hopper attached with the dryer. The total operating time was 10.25 minutes that was equivalent to a drying rate of 0.88 pounds per hour per square feet (8.292 kg/hour/m$^2$). The analytical results of the product are listed in Table 1. The sample potency is determined by the standard method stated in US pharmacopoeia. The content of residual solvents (ethanol and methanol) is determined by gas chromatography. The product color is determined by a light UV-Vis spectrophotometer. A 25% (g/mL) solution of the dried product in water is used and the product specifications require the absorbency less than 0.15 A.U. The result is 0.06 A.U.(Table 1).

Example 2

Drying at Reduced Pressure with a Double Drum Dryer

The same double drum dryer and the same batch of heparin sodium solution as in the Example 1 were used. The procedure is same as in the Example 1 except the dryer was operated with the rotating speed of drums at 3 R.P.M., a steam pressure at 50 psig (3.45 bar, steam temperature at 148° C.), a drum gap at 0.009 inch (0.229 mm), a reduced processing pressure at 64 mmHg. The temperature of solution fed was ambient temperature. 0.26 lbs (117.9 g) of the dried solid form of heparin sodium was obtained from one liter of the solution in 7.5 minutes corresponding to a drying rate of 1.04 pounds per hour per square feet (10.152 kg/hour/m$^2$). The analytical results of the product were listed in the Table 1 with the same analytical methods used in Example 1.

Example 3

Control Experiment, Drying with the Standard Process

The sample solution of heparin sodium came from the same parent solution as used in Examples 1 and 2. The solution was first treated with about 750 mL of SDA-3A alcohol per liter of the solution to precipitate the heparin sodium. Then the supernatant liquid was decanted. The remaining pasty suspension was dehydrated with SDA-3A alcohol by adding approximately 8 times the weight of heparin sodium. The supernatant liquid was decanted. This dehydration step was repeated two more times by adding the same ratio of SDA-3A alcohol. Then the precipitate was dried with a tray dryer under vacuum between 40 and 75° C. for over 60 hours, milled and re-dried for an additional day. The analytical methods used are same as above in Example 1. The results are listed in Table 1.

TABLE 1

Analytical Results of Dried Purified Heparin

| ITEM | POTENCY | RESIDUAL MOISTURE (LOD) | RESIDUAL ETHANOL/ METHANOL | ABSORBANCE at 400 nm |
|---|---|---|---|---|
| EXAMPLE 1 | 162 u/mg | 3.2% | <0.1%/<0.1% | 0.06 A.U. |
| EXAMPLE 2 | 160 u/mg | 4.8% | <0.1%/<0.1% | 0.05 A.U. |
| EXAMPLE 3 | 157 u/mg | 0.9% | 8%/<0.1 | 0.04 A.U. |

Example 4

Drum-drying of Glycosoamino-glycan Solutions Containing Over 90% of Heparin by Weight and the Remaining as Dermatan Sulfate and Other Impurities ("Crude Heparin")

A solution (1.5 liter) of crude Heparin 9.5% (by weight) and 5% (by weight) of SDA-3A alcohol in water at ambient temperature was loaded into a Bufflovac 6"×8" double drum dryer with a rotating speed of 3 RPM, a steam pressure 75 psig (5.1 bar and steam temperature of 161 deg. C.), a drum gap of 0.006 in (0.15 mm) and a pressure in the dryer at atmospheric pressure. Dried crude Heparin powder (60 grams) was collected in the hopper attached with the dryer. The total operating time was 10 minutes. The analytical results of the product are listed in the Table 2. The sample potency is determined by the standard method described in the U.S. Pharmacopeia. The residual Ethanol and Methanol in the product is determined by gas chromatography. The product color is determined by UV-Vis spectrophotometer. A 1% solution (g/ml) of the drum-dried product in water was used in this case as the crude Heparin has higher absorbance due to impurities present at this intermediate stage in Heparin manufacturing process. The results are listed in Table 2. As can be seen from the data of Table 2, the potency of the dried crude heparin of this example is comparable to that of purified heparin dried by the standard process as in Example 3.

The sample of dried crude heparin was then purified in the laboratory using standard chemical purification steps and lyophilized. The analytical results of the purified heparin derived from the drum dried-crude heparin are shown in Table 2A.

TABLE 2

Analytical Results of Dried Crude Heparin

| ITEM | POTENCY | RESIDUAL MOISTURE (LOD) | RESIDUAL ETHANOL/ METHANOL | ABSORBANCE at 400 nm (1% solution) |
|---|---|---|---|---|
| EXAMPLE 4 | 151 u/mg | 2.8% | <0.5% | 0.07 A.U. |

TABLE 2A

Analytical Results of Purified Heparin from Drum Dried-Crude Heparin

| ITEM | POTENCY | RESIDUAL MOISTURE (LOD) | RESIDUAL ETHANOL/ METHANOL | ABSORBANCE at 400 nm (1% solution) |
|---|---|---|---|---|
| EXAMPLE 4 | 175 u/mg | 0.1% | <0.6% | 0.05 A.U. |

What is claimed is:

1. A method for processing a solution containing heparin in a solvent or a mixture of solvents to a dry solid form of heparin characterized by the use of a drum dryer at atmospheric pressure or under vacuum and at a suitable drying temperature.

2. The method of claim 1 wherein the heparin is a free heparin; or a salt of heparin with an alkali metal, or an alkaline earth metal, or ammonium, or a quaternary ammonium, or tertiary amine, or any organic base; or a complex of heparin with an inorganic or organic salt such as an ammonium salt, or a quaternary ammonium salt, or a tertiary amine salt.

3. The method of claim 1 wherein the heparin is heparin sodium.

4. The method of claim 2 wherein the heparin is heparin sodium.

5. The method of claim 1 wherein the solvent of the heparin solution is water or water with water miscible organic solvents, or alcohols.

6. The method of claim 5 wherein the organic solvent is an alcohol or a mixture of alcohols.

7. The method of claim 5 wherein the organic solvent is acetone.

8. The method of claim 1 wherein the drum dryer is a double drum dryer.

9. The method of claim 1 wherein the drum dryer is a single drum dryer.

10. The method of claim 1 wherein the drying temperature is between 20–210° C.

11. The method of claim 1 wherein the drying temperature is between 130–170° C.

12. The method of claim 1 wherein the pressure is between 0.01 mmHg to atmospheric pressure.

13. The method of claim 11 wherein the pressure is atmospheric pressure.

14. The method of claim 1, wherein the dry solid form of heparin is produced in less than 1 minute from initial contact of the solution containing heparin with a drum.

15. The method of claim 1, wherein the dry solid form of heparin is produced in less than 30 seconds from initial contact of the solution containing heparin with a drum.

16. The method of claim 1 wherein the dry solid form of heparin has a potency of at least 140 n/mg.

17. The method of claim 1 wherein the dry solid form of heparin has a potency of at least 160 u/mg.

* * * * *